United States Patent [19]
Capra et al.

[11] Patent Number: 5,201,709
[45] Date of Patent: Apr. 13, 1993

[54] SINGLE USE, SELF DESTRUCTING DISPOSABLE SYRINGE

[76] Inventors: Nicholas G. Capra, 2200 De Forest Ave., East Hanover, N.J. 07936; Kirk G. McElney, 206 Euclid, Long Beach, Calif. 90803; James D. Pauls, Sr., 520 Brickell Key Dr., Penthouse #4, Miami, Fla. 33131

[21] Appl. No.: 825,790

[22] Filed: Jan. 21, 1992

Related U.S. Application Data

[63] Continuation of Ser. No. 367,143, Jun. 16, 1989, abandoned.

[51] Int. Cl.$^5$ ............................................. A61M 5/32
[52] U.S. Cl. ........................................ 604/110; 604/218
[58] Field of Search ................ 604/110, 187, 218, 228

[56] References Cited

U.S. PATENT DOCUMENTS

| | | | |
|---|---|---|---|
| 3,951,146 | 4/1976 | Chiquiar et al. | |
| 4,252,118 | 2/1981 | Richard et al. | 604/228 X |
| 4,367,730 | 1/1983 | Legendre et al. | |
| 4,391,272 | 7/1983 | Staempfli | 604/110 |
| 4,493,703 | 1/1985 | Butterfield | 604/110 |
| 4,731,068 | 3/1988 | Hesse | 604/110 |
| 4,781,684 | 11/1988 | Trenner | 604/110 |
| 4,863,427 | 9/1989 | Cocchi | 604/110 |

*Primary Examiner*—John D. Yasko
*Attorney, Agent, or Firm*—Dennis H. Lambert

[57] ABSTRACT

A disposable hypodermic syringe which is self-destructing upon a single use has an elongate, cylindrical barrel with an adapter means on one end for attachment of a needle and an open other end. A plunger and piston carried thereby are reciprocable in the barrel. The improvement comprises releasable, interengaged flange means on the piston and plunger for holding the piston and plunger assembled together during initial retraction of the plunger and piston in the barrel but which is operative to disengage the mutually engaged flange means upon forward movement of the plunger in the barrel, whereby subsequent retraction of the plunger results in separation of the piston and plunger, rendering the syringe inoperative for subsequent reuse.

14 Claims, 7 Drawing Sheets

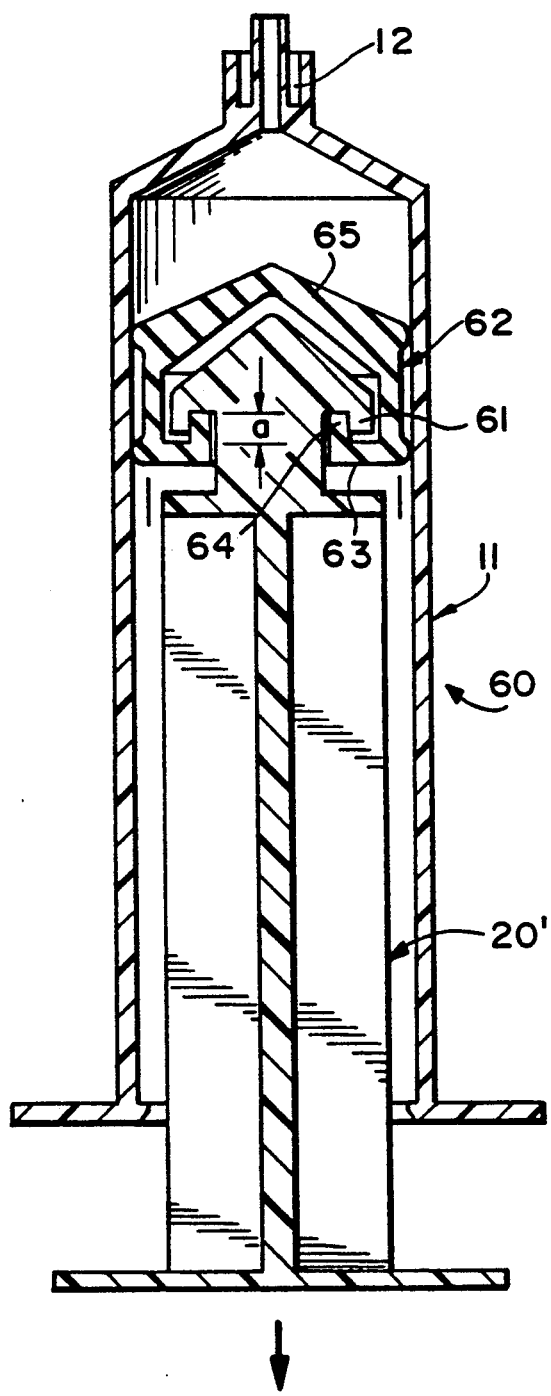
FIG. 6
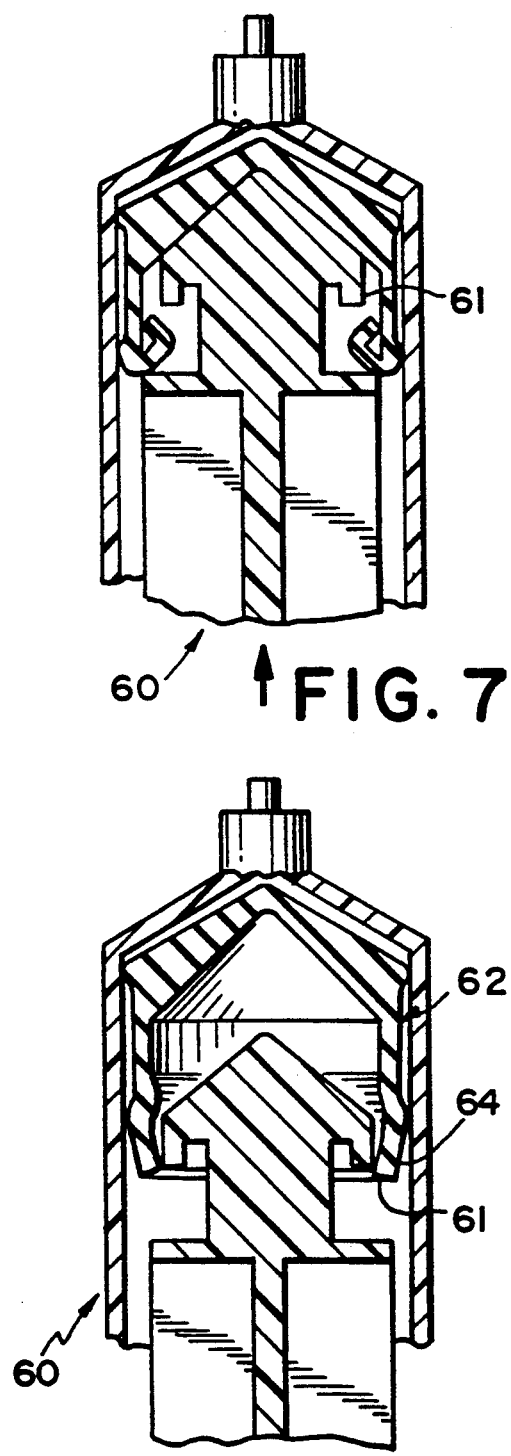
FIG. 7
FIG. 8

SINGLE USE, SELF DESTRUCTING DISPOSABLE SYRINGE

This is a continuation of copending application Ser. No. 07/367,143 filed on Jun. 16, 1989 now abandoned.

FIELD OF THE INVENTION

This invention relates to syringes, and especially to a disposable, non-reusable, self-destructing hypodermic syringe for use in the intravenous administration of fluids.

DESCRIPTION OF THE PRIOR ART

Hypodermic syringes are commonly used for the intravenous administration of fluids. When used in medical facilities such as hospitals, doctor's offices and the like, these syringes are generally properly disposed of after a single use. However, in some instances syringes are illegally obtained or are not properly rendered inoperative or disposed of after use. The danger then exists that these syringes will be reused and/or used by more than one person.

Although the medical community has long used disposable syringes, intravenous drug abusers consistently use the same syringe over-and-over again and share them with other drug abusers. This practice has led to the rapid spread of the HIV virus and Hepatitis in the drug user population.

Acquired Immune Deficiency Syndrome (AIDS) is now recognized as an epidemic of global proportion. In addition, there is an increasing recognition of a broad spectrum of severe HIV associated diseases, including pneumonia, endocarditis and pulmonary tuberculosis, particularly among intravenous drug abusers. Intravenous drug use accounts for most AIDS related diseases in heterosexual men, women and children. Unfortunately, the existence of AIDS among intravenous drug abusers involves not only the drug abusers themselves, but also their sex partners and those children born to the drug users or their sex partners.

As the AIDS related diseases continue to grow, particularly in groups associated with intravenous drug abuse, it is important that preventive measures be taken to prevent the spread of AIDS among the intravenous drug abuser population. Since the major cause of spread of these diseases is through the repeated and/or shared use of contaminated hypodermic syringes and needles, a significant preventive measure would be the elimination of the ability of intravenous drug abusers to acquire syringes that could be used more than one time.

Examples of some prior art efforts to provide nonreusable syringes are disclosed in U.S. Pat. No. 3,478,937, 3,951,146, 4,367,738, 4,391,272, 4,493,703, 4,731,068 and 4,781,684. Most of these patented devices involve some type of catch mechanism which becomes engaged upon full or partial travel of the syringe piston to lock the piston in place and prevent either its withdrawal or its insertion into the syringe barrel. Other devices disclosed in these patents include pistons which become separated from the plunger or stem after an operating cycle to eject a fluid from the syringe. For instance, patents 4,391,272, 4,731,068 and 4,781,684 disclose arrangements in which both some type of catch mechanism and a separable piston and stem structure are used. All of the prior art devices known to applicant are either excessively complicated and expensive in construction or are not adequately reliable in operation. Moreover, it is possible in some of these devices to reassemble them after a single use, whereby they may then be repeatedly used again.

Accordingly, it would be desirable to have a disposable hypodermic syringe that is reliable in operation, simple and economical in construction, and that is not capable of being reused after a single use.

SUMMARY OF THE INVENTION

The disposable syringe of the invention comprises a cylindrical syringe barrel having a suitable conventional fitting on one end, such as a luer lock adapter, for attachment of a needle, and an opposite open end. A plunger or stem is reciprocable in the barrel and carries a piston on its inner end for developing vacuum or pressure, depending upon the direction of movement of the piston, as the plunger is reciprocated in the barrel. In accordance with the invention, the plunger and piston are of substantially conventional construction, modified only to the extent that a releasable connection is provided between them, whereby the piston will become separated from the plunger after only a single use of the syringe, disabling the syringe from further use. In a preferred form of the invention, the rear portion of the piston is formed with a skirt having an inturned flange which engages behind a lip on the forward end of the plunger. A collar is engaged over the skirt to hold the skirt and flange in operative position during retraction of the plunger and piston in the barrel, but when the plunger and piston are pushed forwardly in the barrel to expel fluid from the barrel the collar remains in its retracted position due to frictional engagement between the collar and inner barrel wall. Thus, the skirt and flange are permitted to flex outwardly out of operative engagement with the lip on the plunger, and when the plunger is again retracted relative to the barrel, the plunger separates from the piston, leaving the piston in the forward end of the barrel and rendering it incapable of further use. Attempts to reassemble the syringe for further use are thwarted by providing means in the barrel to prevent withdrawal of the plunger outwardly through the open end, and the end wall of the plunger may be made thin so that efforts to push the piston rearwardly in the barrel by use of a pin inserted through the luer lock adapter will merely pierce the piston. In other forms of the invention, the collar is eliminated and the piston is held assembled to the plunger by interengaged flanges on the piston and plunger. Forward movement of the plunger and piston in the barrel is possible, whereby a medicament may be intravenously administered with the syringe, but reverse movement of the plunger results in separation of the plunger and piston. These forms of the invention have particular suitability for pre-filled syringes, for example. In all forms of the invention, the interengaged flanges on the piston and plunger may be constructed so that limited forward and reverse movements may be made without separation of the piston from the plunger. This feature is useful when it is desired or necessary to effect small forward movement of the plunger and piston to expel air which has been drawn into the barrel when aspirating a fluid to be administered. In one form of the invention yieldable buffers are provided between the piston and plunger which resist disengagement of the interengaged flanges during the expulsion of air, but which are collapsed during the expulsion of liquid so that the flanges become disengaged and the syringe is rendered inoperable.

BRIEF DESCRIPTION OF THE DRAWINGS

The foregoing and other objects and advantages of the invention will become apparent from the following detailed description when considered with the accompanying drawings, wherein like reference characters designate like parts throughout the several views, and wherein:

FIG. 6 is an enlarged, longitudinal sectional view of a second form of syringe according to the invention, showing the parts in operative, assembled relationship to one another;

FIG. 7 is a fragmentary sectional view of the syringe of FIG. 6, showing the relationship of the parts following forward movement of the plunger and piston in the barrel;

FIG. 8 is a view similar to FIG. 7, showing the relationship of parts when the plunger is retracted in the barrel following forward movement thereof;

DETAILED DESCRIPTION OF THE PREFERRED EMBODIMENTS

Figure 1:
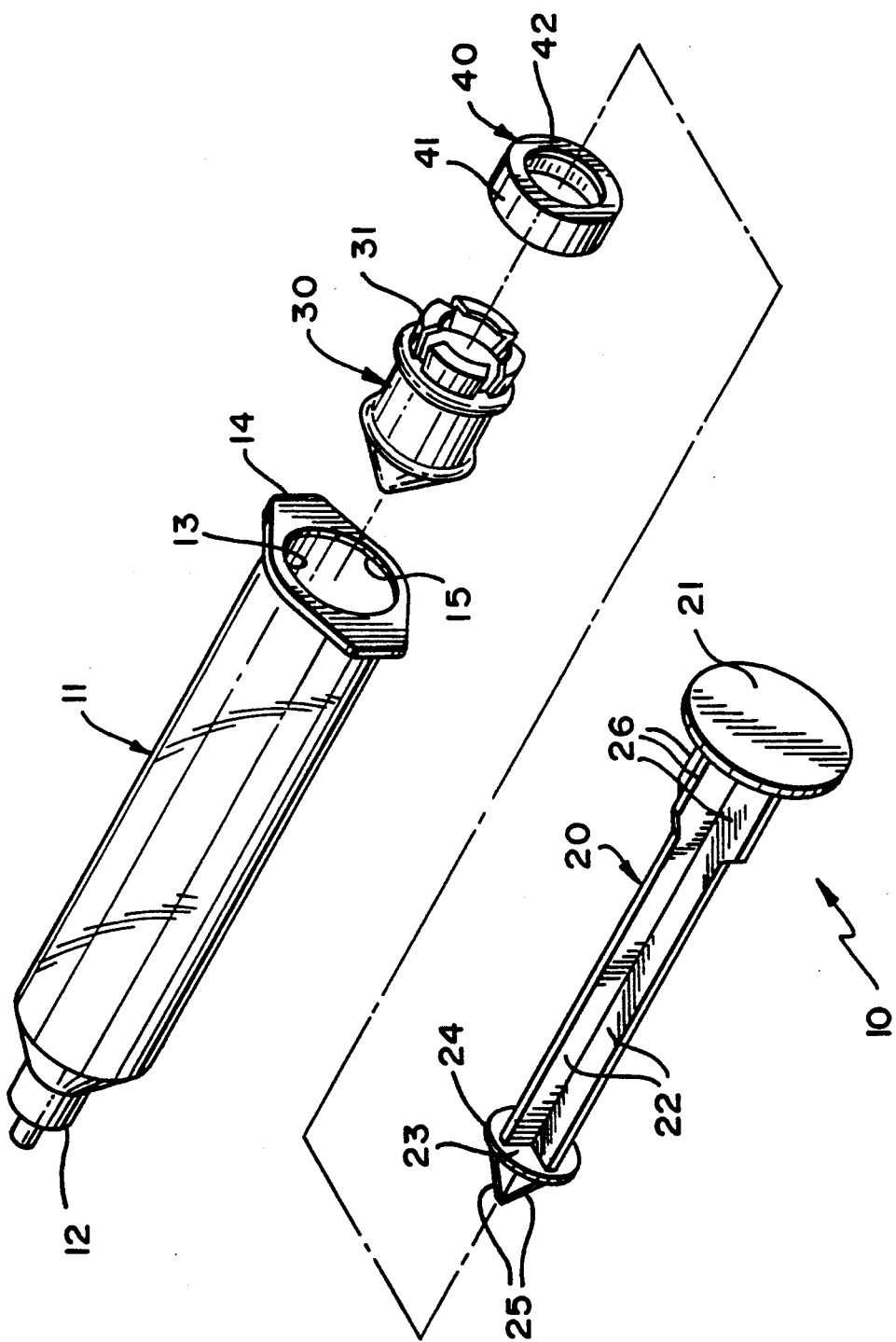
FIG. 1 is an exploded perspective view of a first form of syringe according to the invention.

Referring more specifically to the drawings, a first form of the syringe according to the invention is shown generally at 10 in FIGS. 1-5. In this form of the invention, a cylindrical barrel 11 of conventional construction has a needle adapter, such as luer lock 12, on one end for attachment of a needle. The other end 13 is open and has outwardly directed finger-engaging flanges 14 for facilitating manipulating of the syringe. A radially inwardly directed flange or rib 15 is also formed in the open end of the barrel to prevent withdrawal of the plunger from the barrel as described hereinafter.

A plunger or stem 20 of substantially conventional construction is inserted into the barrel through the open end thereof, and has a disc-shaped end 21 adapted to be engaged with the finger of the user for reciprocating the plunger in the barrel. The body of the plunger comprises a plurality of radial flanges or webs 22, terminating at their forward ends in a second disc-shaped end 23 having a radially enlarged lip 24 projecting radially outwardly beyond the webs 22. A plurality of triangularly shaped webs 25 extend forwardly of the end 23 and define a generally conically shaped tip on the plunger. As seen best in FIG. 2, the webs 22 extend nearly to the inner surface of the barrel at their rearward ends 26, but are spaced therefrom over the remainder of their lengths.

A piston 30 made of suitable elastomeric material is releasably attached to the forward end of the plunger via an axially rearwardly extending skirt 31 having an inturned annular flange 32 on its rearward end engaged behind the lip 24 on the plunger. A rearward end surface 33 of the piston is shaped complementally to the conical tip on the plunger, and this surface is spaced slightly forwardly from the tip end of the plunger when the flange 32 is engaged behind the lip 24, as shown exaggerated in FIG. 2. This spacing facilitates assembly of the piston to the plunger.

An annular collar 40 is telescopically engaged over the skirt and has a cylindrical wall 41 with a predetermined length L, which may approximate the length of the skirt, and a radially inturned flange 42 which engages beneath the inturned flange 32 on the piston skirt. When thus assembled, the piston and plunger are held securely together and may be retracted rearwardly in the barrel as depicted in FIG. 2.

The wall 41 of the collar has a tight sliding fit in the bore of the barrel and may be pulled rearwardly upon retraction of the plunger and piston because of engagement of the lip 24 on the forward end of the plunger with the inturned flange 32 on the piston and engagement of that flange with the inturned flange 42 on the collar. In other words, the lip of the plunger cannot be pulled rearwardly through the opening defined by the inturned flange on the collar due to the wedging engagement of the flange on the piston between the flange on the collar and the lip on the plunger.

Figure 3:
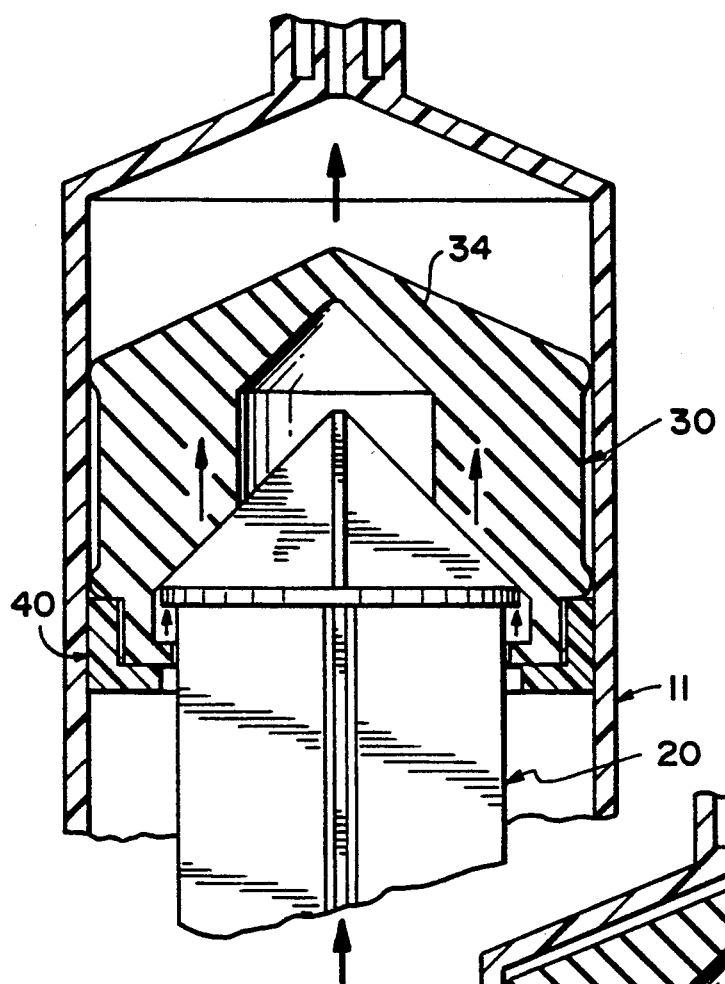
FIG. 3 is a fragmentary sectional view similar to FIG. 2, showing the parts during an initial forward movement of the plunger and piston in the barrel.
Figure 4:
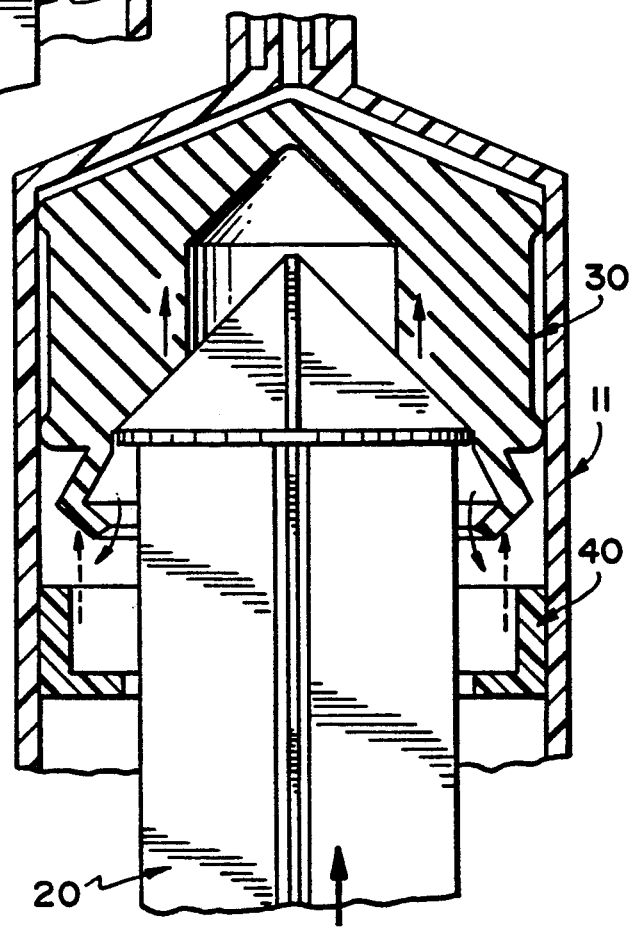
FIG. 4 is a view similar to FIG. 3, showing the relationship of the parts after continued forward movement of the plunger and piston.

However, the skirt 31 and flange 32 on the piston axially slit at circumferentially spaced locations 43, defining a plurality of circumferentially spaced segments. These segments are molded with a natural radial outward bias or memory, whereby they spring or flex outwardly as shown in FIG. 4 when they are released from the restraining effect of the collar. This occurs when the plunger is pushed forwardly in the barrel as depicted in FIGS. 3 and 4, resulting in lodgement of the collar in the bore of the barrel while the plunger and piston continue their forward movement. Any effort to retract the piston in the barrel results in disengagement of the plunger from the piston as shown in FIG. 5.

Figure 2:
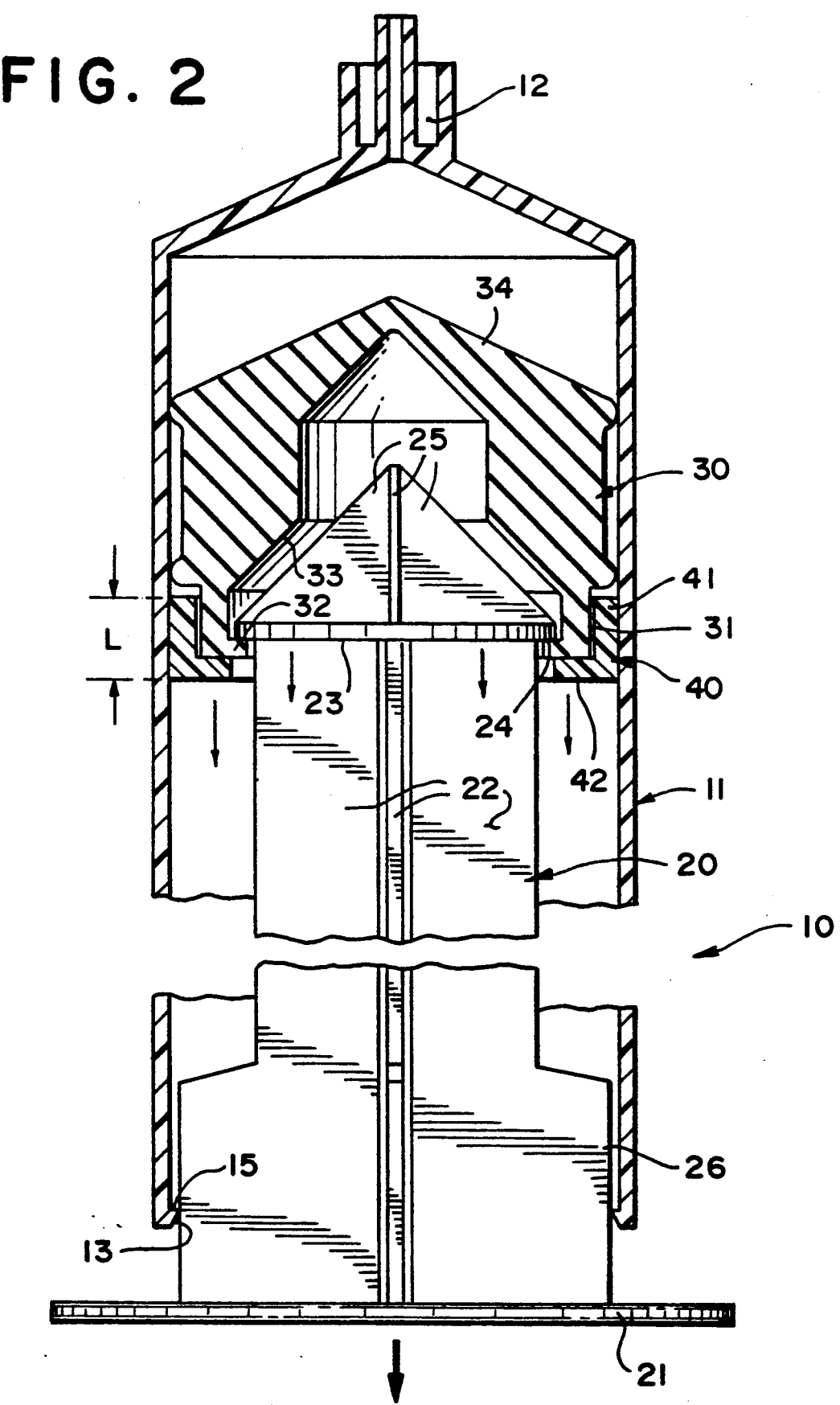
FIG. 2 is a greatly enlarged longitudinal sectional view of the syringe of FIG. 1, showing the parts in operative assembled relationship.
Figure 5:
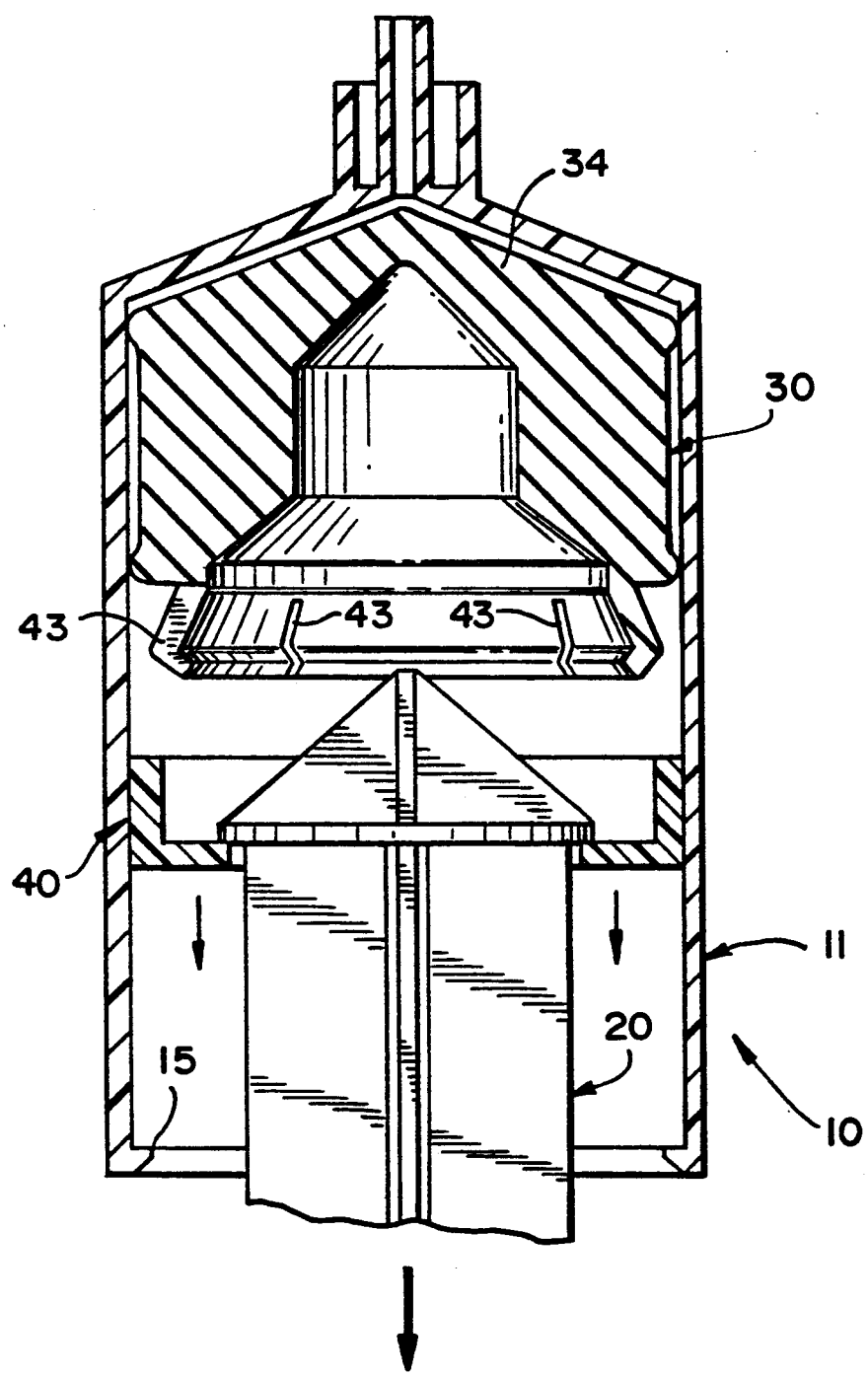
FIG. 5 is a view similar to FIG. 4, showing the relationship of the parts when reverse movement of the plunger is effected following forward movement thereof to expel a fluid from the syringe.

Complete withdrawal of the plunger and collar through the open end of the barrel is prevented by an annular stop rib or flange 15 formed in the inner surface of the open end of the barrel (see FIGS. 2 and 5).

To thwart efforts to move the piston to a retracted position in the barrel by inserting a thin instrument such as a paper clip or the like through the luer lock adapter, the end wall 34 of the piston may be made relatively thin, whereby it will be pierced by such instrument, rather than being pushed rearwardly in the barrel.

If desired, the length L of the cylindrical wall 41 on the collar may be made sufficiently long to enable limited forward movement of the plunger and piston in the barrel without effecting disengagement of the piston from the plunger. For instance, a wall having a length of one inch would enable that much forward travel of the piston and plunger without becoming disengaged. This would enable any air which might be present in the barrel to be expelled prior to making an injection with the syringe. Obviously, other lengths could be selected to give the desired result, even a length permitting no forward movement without effecting disengagement of the piston from the plunger. This design could be implemented, for example, on pre-filled syringes.

A second form of the invention is shown generally at 60 in FIGS. 6–8. In this form of the invention, the collar is eliminated and the forward or tip end of the plunger is formed with an annular, axially rearwardly extending cylindrical flange 61. The piston 62 is also modified to the extent that the skirt is eliminated and the rear wall 63 of the piston has an annular, forwardly extending cylindrical flange 64 thereon which is adapted to engage behind the flange 61 on the plunger. The normal, operative position of the parts is depicted in FIG. 6 The rigidity and strength of the flange 64 and wall 63 on the piston are selected relative to the frictional resistance to sliding movement of the piston in the barrel that the piston may be drawn rearwardly in the barrel by the plunger as shown in FIG. 6. However, the wall and flange are molded with a memory such that their normal, at-rest position is as shown in FIG. 7. Consequently, when the plunger is pushed forwardly in the barrel of the syringe as shown in FIG. 7, the flanges on the piston and plunger move axially relative to one another and become disengaged. Subsequent rearward movement of the plunger in the barrel results in stripping of the plunger end out of the piston, as shown in FIG. 8, rendering the device inoperable for reuse. As with the previously described form of the invention, the end wall 65 of the piston may be made thin so that efforts to push the piston rearwardly in the barrel by inserting an instrument through the needle adapter will merely result in puncturing or piercing the piston.

Figure 9:
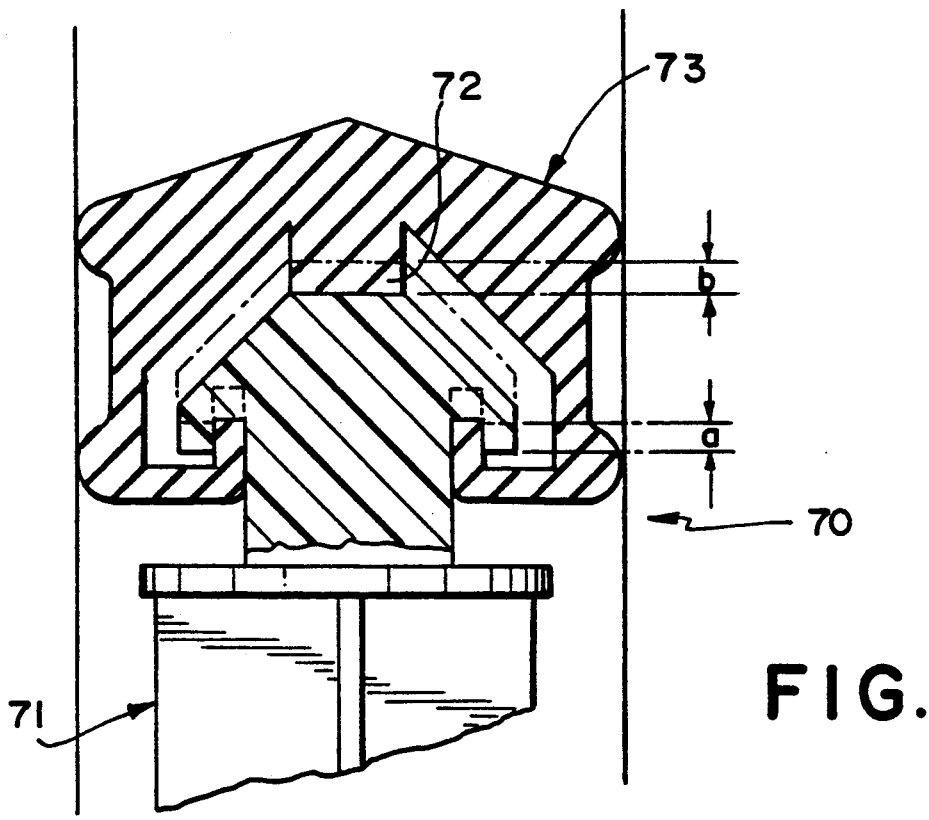
FIG. 9 is an enlarged, fragmentary sectional view of a third form of the invention, wherein a yieldable buffer is provided between the piston and plunger to permit the expulsion of air from the syringe without disengaging the piston from the plunger.

A third form of the invention is shown generally at 70 in FIG. 9. In this form of the invention, the plunger 71 is constructed identically to that form of the invention shown in FIGS. 6–8. However, a yieldable buffer 72 is formed in a rear surface portion of the piston 73 for engagement against the end of the plunger to hold the piston and plunger in their normal, operative positions as shown in full lines in FIG. 9. The buffer is designed with sufficient rigidity to resist collapse when the plunger is pushed forwardly to expel air from the syringe, but will collapse or yield when the added resistance of liquid is encountered. In this event, the buffer collapses or yields a distance "b", which is calculated to be greater than the distance "a" through which the flanges on the piston and plunger remain engaged. Consequently, air may be expelled from the syringe by forward movement of the plunger and piston without disengaging the piston from the plunger, but when the syringe is used to expel liquid the resistance of the buffer is overcome and the piston becomes separated from the plunger, disabling the syringe for subsequent use.

Figure 10:
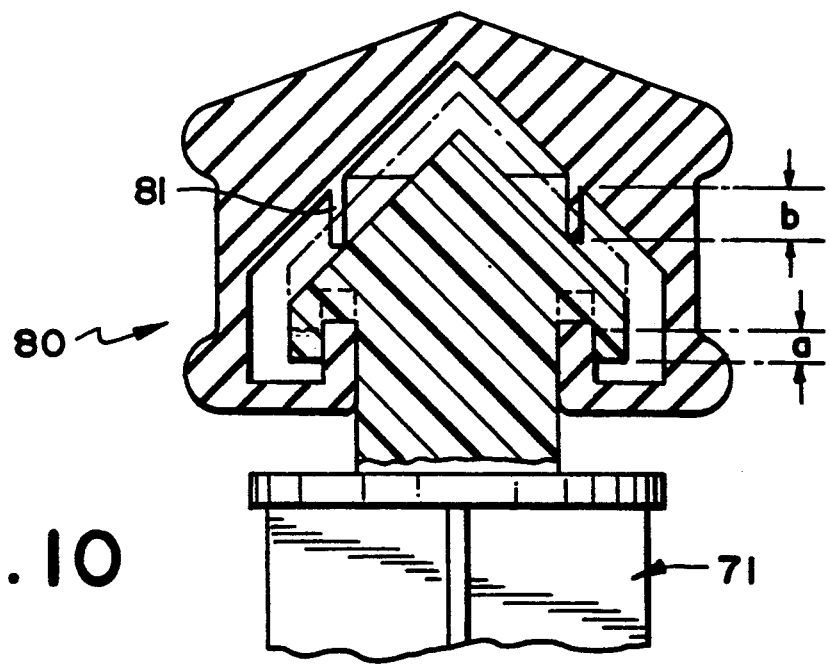
FIG. 10 is a view similar to FIG. 9, showing a fourth form of the invention in which a variation of the yieldable buffer is provided.

A similar arrangement is shown generally at 80 in FIG. 10, wherein an annular, rearwardly projecting cylindrical wall 81 in the piston forms the buffer. In all other respects, this form of the invention functions exactly the same as that in FIG. 9.

Figure 12:
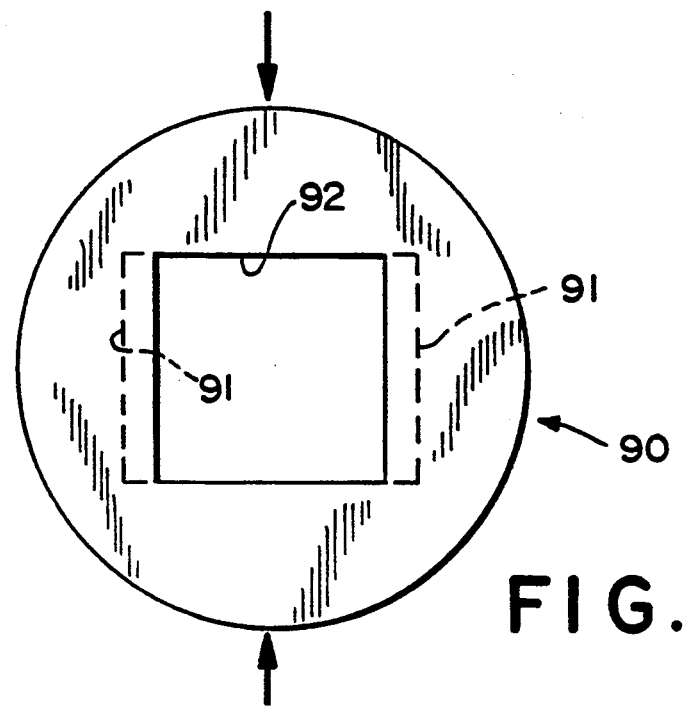
FIG. 12 is a view similar to FIG. 11, showing a variation of the means of attachment of the piston to the plunger.
Figure 11:
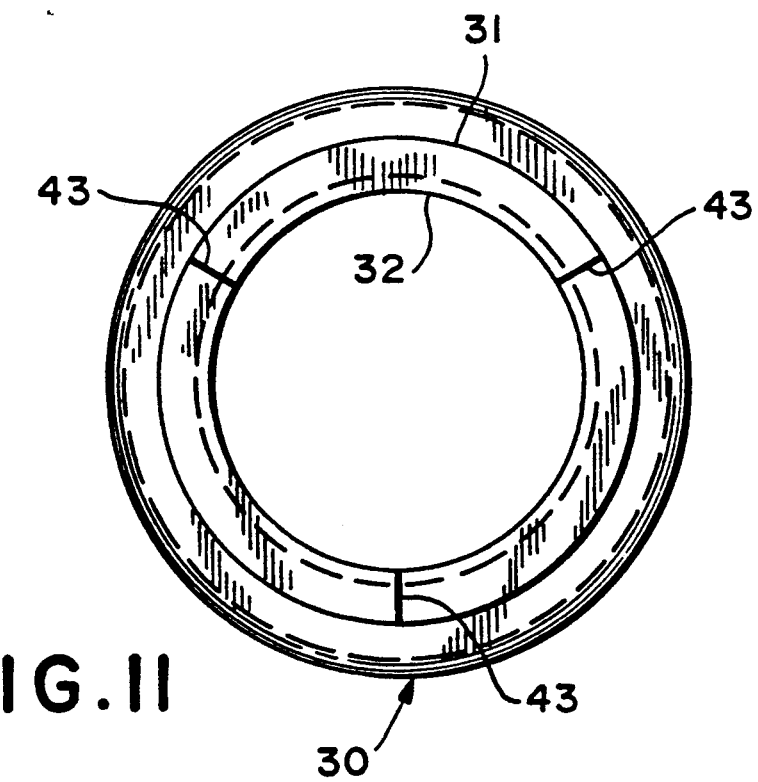
FIG. 11 is an end view of a piston suitable for use in any of FIGS. 1-10, showing how the piston skirt is slit to facilitate assembly and disengagement relative to the plunger.

FIGS. 11 and 12 show variations in the structure which may be employed in the piston for attachment thereof to the plunger. In FIG. 11, for example, the piston 30 as used in FIGS. 1–5 is slit radially through the skirt 31 and flange 32 to facilitate assembly of the piston to the plunger and also to permit the skirt and flange to more readily flex outwardly out of engagement with the plunger. An alternative construction is shown at 90 in FIG. 12, wherein the inturned flanges 91 on the piston are rectilinear and are formed on only two sides of the rectilinear opening 92 formed or defined between the flanges. The plunger end (not shown) would be similarly rectilinearly formed. To assemble the piston to the plunger, the sides of the piston opposite the sides containing the flanges 91 would be squeezed inwardly, as represented by the arrows, thus buckling the flanges outwardly for receipt therebetween of the end of the plunger.

Although the invention has been described with reference to particular embodiments, it is to be understood that these embodiments are merely illustrative of the application of the principles of the invention. Numerous modifications may be made therein and other arrangements may be devised without departing from the spirit and scope of the invention.

We claim:

1. In a hypodermic syringe having an elongate, cylindrical barrel with an adapter means on one end for attachment of a needle and an open other end, and in which a plunger and piston carried thereby are reciprocable, the improvement comprising:

releasable, interengaged flange mans on the piston and plunger for holding the piston and plunger assembled together during initial retraction of the plunger and piston in the barrel, the flange means on the piston including a cylindrical skirt projecting coaxially with the end of the plunger, said flange means including an annular, radially inwardly projecting flange on the skirt; and a retaining collar telescopically engaged over the skirt, holding it and the associated flange in operative engagement with the flange on the plunger, said collar being slidably engaged in the barrel with sufficient frictional resistance that forward movement of the plunger and piston in the barrel results in said collar becoming lodged in the barrel and disengaged from the skirt, whereby the flange means on the piston can become disengaged from the flange means on the plunger, and whereby subsequent retraction of the plunger results in separation of the piston and plunger, rendering the syringe inoperative for subsequent reuse.

2. In a hypodermic syringe having an elongate, cylindrical barrel with an adapter means on one end for attachment of a needle and an open other end, and in which a plunger and piston carried thereby are reciprocable, the improvement comprising:

releasable, interengaged means on the piston and plunger for holding the piston and plunger together during initial retraction of the plunger and piston in the barrel;

a resiliently yieldable buffer axially engaged between the piston and plunger, said buffer having sufficient rigidity as not to be compressed upon forward movement of the plunger against the piston to expel air from the barrel, but being yieldable when the increased resistance of liquid is encountered during use of the syringe to inject a liquid, whereby limited forward axial movement of the plunger and piston in the barrel may be accomplished without disengaging the piston from the plunger;

means for disengaging the mutually engaged means upon extensive forward axial movement of the plunger in the barrel, whereby subsequent retraction of the plunger results in separation of the piston and plunger, rendering the syringe inoperative for subsequent reuse.

3. A syringe as claimed in claim 1, wherein:
an annular stop flange or rib is formed on an inner surface of said open end, said stop flange cooperating with said plunger to prevent its complete withdrawal from the barrel.

4. A syringe as claimed in claim 3, wherein: the cylindrical skirt and associated radially inwardly projecting flange have a radially outward bias, whereby when the collar becomes detached therefrom they flex outwardly away from the flange on the plunger.

5. A syringe as claimed in claim 2, wherein:
the flange means on the piston and the plunger include mutually interengaged axially directed flanges, said piston and said plunger being normally axially spaced from one another except where said flanges engage, whereby limited relative axial movement is permitted between the plunger and the piston before the flanges become disengaged from one another.

6. A syringe as claimed in claim 5 wherein:
the flange on the piston has a natural bias in a direction tending to disengage from the flange on the plunger, whereby when the plunger and piston are moved axially relative to one another upon forward movement of the plunger in the barrel, the flange on the piston flexes out of alignment with the flange on the plunger, resulting in the piston becoming separated from the plunger upon subsequent axial movement of the plunger in the opposite direction.

7. A syringe as claimed in claim 2, wherein: the buffer comprises a rod-like button on the piston projecting axially into contact with the forward end of the plunger.

8. A syringe as claimed in claim 2, wherein:
the buffer comprises a thin, cylindrical wall projecting rearwardly from the piston into contact with the forward end of the plunger.

9. A hypodermic syringe: comprising:
a cylindrical barrel with an adapter at a forward end for attachment of a needle, and an opposite rearward open end;
a plunger slidably disposed within said cylindrical barrel, said plunger having a forward end with a radially extending enlarged lip;
an elastomeric piston slidably disposed within said cylindrical barrel and releasably attached to said forward end of said plunger by an axially rearwardly extending skirt having a radially inwardly extending annular flange for engaging with said radially extending enlarged lip of said plunger; and
an annular collar resistant to sliding disposed within said cylindrical barrel and telescopically engaging and extending around said axially rearwardly extending skirt of said piston, said annular collar having a radially inwardly extending annular flange;
whereby said axially rearwardly extending skirt of said piston engages with said radially inwardly extending annular flange of said annular collar to retain said piston on said plunger by said radially inwardly extending annular flange of said piston engaging with and retaining said radially extending enlarged lip of said plunger upon withdrawing said plunger from said cylindrical barrel; and
whereby said annular collar disengages from said piston upon forward movement of said plunger due to said annular collar resisting forward movement, operationally detaching said radially inwardly extending annular flange of said piston from said radially extending enlarged lip of said plunger and thus detaching said plunger from said piston upon another attempt to withdraw said plunger from said cylindrical barrel.

10. A hypodermic syringe according to claim 9, wherein said axially rearwardly extending skirt and said radially inwardly extending annular flange of said piston are slit at circumferentially spaced locations so as to define a plurality of circumferentially spaced segments.

11. A hypodermic syringe according to claim 10, wherein said segments are molded with a natural outward bias, whereby said segments flex outwardly when released from a restraining effect of said annular collar.

12. A hypodermic syringe, comprising:
a cylindrical barrel with an adapter at a forward end for attachment of a needle, and an opposite, open rearward end;
a plunger slidably disposed within said cylindrical barrel, said plunger having a forward end with an annular, axially rearwardly extending cylindrical flange;
a piston slidably disposed within said cylindrical barrel and releasably attached to said forward end of said plunger by a rear wall on the piston having an annular, axially forwardly extending cylindrical flange engaged behind the flange of said plunger;
the rigidity and strength of said flange of said piston being selected relative to the frictional resistance to sliding movement of said piston within said barrel so that said piston may be drawn rearwardly in said barrel by said plunger without detaching from said piston;
said plunger and said piston having limited axial movement relative to one another such that upon forward movement of the plunger in the barrel, said rearwardly extending flange on the plunger becomes axially displaced from registry with the forwardly extending flange on the piston; and
said rear wall and said forwardly extending flange on the piston being molded with a memory such that said flange has a natural outward bias, so that when the flange on the piston is out of registry with the flange on the plunger due to axial displacement between the piston and the plunger, the forwardly extending flange moves radially outwardly to provide clearance for said rearwardly extending flange on the plunger to move therepast upon subsequent rearward movement of the plunger in the barrel, whereby when said plunger is pushed forwardly within said barrel and subsequently withdrawn in said barrel, the piston becomes disengaged from the plunger, thus preventing withdrawal of said piston in said barrel upon said subsequent withdrawal of the plunger.

13. A hypodermic syringe according to claim 12, wherein said yieldable buffer is defined by an annular rearwardly projecting cylindrical wall in said piston.

14. A hypodermic syringe according to claim 12, including a yieldable buffer formed in an inner rear surface portion of said piston for engaging with a forward tip of said plunger for resisting relative axial displacement between the plunger and piston when the plunger is pushed forwardly within the barrel to expel air from the barrel, but which collapses or yields to permit axial displacement between the piston and plunger when the piston encounters liquid in the barrel, whereby the piston and plunger are axially displaced relative to one another and become disengaged, preventing subsequent withdrawal of the piston in the barrel.

* * * * *